(12) United States Patent
Thorel

(10) Patent No.: US 6,342,236 B1
(45) Date of Patent: Jan. 29, 2002

(54) COSMETIC PRODUCTS COMPATIBLE WITH CUTANEOUS ECOLOGY

(76) Inventor: Jean-Noël Thorel, 3 rue la Rochelle, 75014 Paris (FR)

( * ) Notice: Subject to any disclaimer, the term of this patent is extended or adjusted under 35 U.S.C. 154(b) by 0 days.

(21) Appl. No.: 09/341,900

(22) PCT Filed: Jan. 20, 1998

(86) PCT No.: PCT/FR98/00100

§ 371 Date: Sep. 21, 1999

§ 102(e) Date: Sep. 21, 1999

(87) PCT Pub. No.: WO98/31337

PCT Pub. Date: Jul. 23, 1998

(30) Foreign Application Priority Data

Jan. 21, 1997 (FR) ............................................. 97 00803

(51) Int. Cl.$^7$ .......................... A61K 7/00; A61K 35/12; A61K 33/00
(52) U.S. Cl. ........................ 424/401; 424/522; 424/600
(58) Field of Search ................................ 424/401, 522, 424/600

(56) References Cited

U.S. PATENT DOCUMENTS 4,863,897 A * 9/1989 Dede et al.

FOREIGN PATENT DOCUMENTS

| EP | 0 210 483 A | 2/1987 |
|---|---|---|
| EP | 0 237 398 A | 9/1987 |
| EP | 0 379 846 A | 8/1990 |
| EP | 0 475 851 A | 3/1992 |
| EP | 0 477 833 A | 4/1992 |
| EP | 0 627 223 A | 12/1994 |
| WO | WO 89 05629 | 6/1989 |
| WO | WO 94 18945 A | 9/1994 |
| WO | WO 97 25023 A | 7/1997 |

* cited by examiner

*Primary Examiner*—Leon B. Lankford, Jr.
*Assistant Examiner*—Susan D. Coe
(74) *Attorney, Agent, or Firm*—Oliff & Berridge, PLC

(57) ABSTRACT

These products are characterised in that they contain for at least 90% by weight, only of constituents biologically compatible with the skin and the skin cells, expressing together interactively at least a topical bioactivity, identical to or different from the bioactivity of at least one constituent biologically compatible with the skin, and providing to said product a composition in stable topical galenic form, practically excluding any excipient biologically non-compatible with the skin other than water.

1 Claim, No Drawings

COSMETIC PRODUCTS COMPATIBLE WITH CUTANEOUS ECOLOGY

The present invention relates to cosmetology, body-hygiene, topical dermotherapeutics and, in general, any product intended for the skin, or for surface parts of the human body, in the region of the epidermis, such as nails and hair.

Traditionally, a cosmetic or dermatological product comprises one or more active principles and an excipient or vehicle in which the active principle(s) is (are) distributed or dispersed, the whole being formulated for topical application, for example in the form of a gel or cream.

The term "active principle" means any compound, any composition or any product which exerts biomechanical, biophysical, physiological or biological activity on the skin, and in particular on the epidermis, and which has any physicochemical form or nature required for the treatment or action chosen or selected with respect to the skin.

The active principle(s) selected, of chemical type, is (are) in the great majority foreign to the skin; cf. EP-0,475,851. In certain cases, these active principles are natural products, i.e. products obtained from products or substances of nature, for example in the plant kingdom, cf. EP-0,477,833. In other cases, these active principles are products or constituents found in the skin; cf. WO-94/18945 and EP-0,627,223.

Moreover, cosmetic or dermopharmaceutical products are known which comprise no excipient or vehicle per se, but in the form of a complex, combining various products; cf EP-0,379,846. In certain examples, one or more components, but not all of them, are natural components; cf. WO-89/05629.

At the present time, to the Applicant's best knowledge, nobody has been concerned, for cosmetic or therapeutic purposes, in the skin, and in particular the epidermis, considered as an ecological medium or system whose equilibrium should be respected, with the exception of certain studies relating only to the ecology of the cutaneous bacterial flora.

This is the subject of the present invention.

In its general aspect, the invention proposes a new generation of cosmetic or corporal hygiene or dermotherapeutic products which comprise, to at least 98% by weight, biodermal constituents, each chosen for their biocompatibility and cytocompatibility with skin cells, and preferably biomimetic with a component of the skin, in particular of the epidermis. These biodermal constituents are chosen and formulated, on the one hand, in order together to express at least one topical biological activity, which is identical to or different from the biological activity of at least one biodermal constituent, and, on the other hand, in order to give the product a composition in topical pharmaceutical form which is stable, as regards the mode of administration considered, for example gel, milk, cream, lotion or make-up remover, for a body hygiene or cosmetic product.

It results from the above definition, by difference with the traditional cosmetic or dermatological products, that it is no longer possible in particular to distinguish between active principle(s) and excipient or vehicle. In practice, a product according to the present invention behaves both as one or more active principles and as an excipient. Furthermore, each biodermal constituent must be considered equally as a constituent of the skin and/or an active principle and/or a pharmaceutical agent, for example a thickener or a surfactant.

The composition of a product according to the present invention in practice excludes any non-biodermal excipient other than water or an aqueous phase.

It results from the above definition that a product according to the present invention cannot be likened to:
one or more biodermal, including biomimetic, active principles formulated in a stable pharmaceutical form, with a traditional excipient or vehicle
a complex of natural products, in general without excipient or vehicle per se, since it in practice comprises, as a whole, specific natural products, i.e. biodermal constituents.

According to the above definition, any product limited to one or more biodermal active principles, distributed in one way or another in water or in an aqueous phase, which is predominant by weight in the total composition of the product is also excluded; this product being, for example, a lotion obtained by dispersing a glycosaminoglycan in an aqueous phase.

Preferably, biodermal constituents which are cytocompatible with the skin represent the entire weight composition of the product considered.

Preferably, each biodermal constituent, which is biomimetic with a component of the skin, has a weight content in the said product (expressed as a weight percentage, for example) which is different from that of the said component in the skin.

By way of example, a product according to the invention comprises two biodermal and biomimetic constituents, the major one of which is a constitutive component of the epidermis and the minor of which is a skin nutrient.

Advantageously, the biodermal constituent is chosen from the biological, mineral, organic or biochemical species or entities of which the epidermis or the dermis is composed. By way of example, one of the biodermal constituents is chosen from skin nutrients.

A product in accordance with the invention is two-phase or single-phase or constitutes several emulsion or non-emulsion phases, to obtain any suitable topical form, for example cream, emulsion, lotion, serum, milk, gel, fluid, etc.

The terms "excipient" and "vehicle" conventionally mean any compound or composition, such as a diluent, dispersant or solvent, which is adapted to form the topical form required, for example a cream, a gel, an oil, a lotion, etc. This composition is completed with various adjuvants that are well known to those skilled in the art, such as wetting agents, astringents, humidifying agents, emollients, etc.

The term "interactive" refers to the property by which the composition of a product according to the invention maintains all the functional biological equilibria of the skin, without inhibiting or exacerbating them, this being in addition to the topical biological activity of the said composition, resulting from the synergistic or non-synergistic biological activity on the skin of one or more biodermal constituents.

A product according to the invention thus has three functions. A first function consists in both protecting and maintaining, or even in restoring, the main biological and physiological cutaneous equilibria. A second function consists in creating a suitable stable pharmaceutical form (milk, cream, etc.). A third function consists in treating the skin by providing it with one or more topical benefits, in particular therapeutic or cosmetic benefits.

The term "pharmaceutical form" means any form or presentation, adapted to the mode of administration selected, which allows the product to exert functional activity on the skin.

The term "biodermal constituent" means any component or product forming part of the composition of the skin, in particular of the epidermis, it being understood that this constituent is considered in isolated form, in a form identical to its natural form, or modified relative to its natural form, but remaining cytocompatible with the skin, irrespective of the method by which it is obtained or produced, in particular by separation from live skin products, by biosynthesis, by a biotechnology process or by genetic recombination.

The term "biologically active" refers to the fact that the component or constituent considered itself displays biological activity in the epidermis, or alternatively participates in any biological process, such as metabolism, in the epidermis.

The term "topical activity" refers to the fact that, globally, the cutaneous interactive base exhibits or manifests, via the topical route, a cosmetic or therapeutic benefit on the skin, for example on the epidermis.

The expression "cytocompatible with the skin" refers to the property by which the biodermal constituent selected has a cytotoxicity of less than 10% with respect to a cell culture of human keratinocytes, i.e. it remains virtually neutral with respect to the cellular viability and morpho-differentiation of the keratinocytes.

This cytocompatibility can be evaluated by means of the following routine test.

Normal human keratinocytes obtained from plastic surgery are cultured in sub-emerged condition in defined medium (MCDB 153) supplemented with 10 ng/ml of an epidermal growth factor, 5 $\mu$g/ml of insulin, 0.1 mM ethanolamine, 0.1 mM phosphoethanolamine and 2% of non-essential amino acids. This medium allows keratinocytes to be cultured without the presence either of serum or of live nourishing cells (3T3 fibroblasts); its low calcium content (0.1 mM) promotes cell growth.

The biodermal constituents are evaluated as regards their capacity to induce cytopathic effects on sub-confluent cultures. The contact times are 6 hours, 12 hours, 24 hours and 36 hours.

The cell viability is measured quantitatively by indirect counting of the live cells after labeling them with a vital dye. The neutral red system (3-amino-7-dimethylamino-2-methylphenasine hydrochloride) measures the activity of passage of the dye across the plasma membrane and of storage in the lysosomes of the viable cells.

The total incorporation of the neutral red is proportional to the number of live cells in culture.

The dye incorporated is extracted with an acetic acid/ethanol solvent and quantified by spectrophotometric measurement. The results are compared qualitatively, relative to culture standards, and are expressed as optical density (OD) and/or percentage of optical density relative to the negative control (untreated culture).

Within the variation limits of the strains used, a percentage of greater than or equal to 90% optical density for a culture placed in contact with the test biodermal constituent, relative to the negative control, indicates that the said constituent is cytocompatible with the skin.

The term "biomimetic" refers to the fact that the biodermal constituent selected has the structure and/or exerts the biomechanical, biophysical, physiological or biological function or activity of any skin component, i.e. of any skin component which can be isolated or separated by fractionating the dermis and/or the epidermis, or alternatively of any component whose existence can be characterized or demonstrated in the dermis and/or the epidermis, or alternatively of any component which can be assimilated by the skin and serve, if need be, as a nutrient for the constituent cells of the skin.

In other words, the skin, as a live biological medium, cannot distinguish between its own biodermal constituents.

Preferably, the biodermal constituents are chosen from biological, inorganic, organic or biochemical species or entities which constitute the skin, irrespective of the effective origin of the constituents brought onto or into the skin.

The biodermal constituents can be chosen from the constituent molecules of the epidermis and of the dermis. By way of example, the following will be selected:

various fluid or solid lipids, such as oleic acid, essential fatty acids, mono-, di- and triglycerides, linoleic acid, squalene, stearic acid or glyceryl monostearate, solid lipids, such as stearic acid, cholesterol, ceramides, cholesterol ester or sulphate, or saturated diglycerides, nucleic acids, mucopolysaccharides such as hyaluronic acid, collagens.

The biodermal constituent can also be chosen from skin nutrients, i.e. compounds or compositions which can be metabolized by skin cells.

By way of example, mention will be made of all the elements, or fragments of foods, which are useful for the metabolism of the skin, such as cutaneous acids, fatty acids, vitamins, peptone, casein, caseinates, immunoglobulin glycoproteins, complex lipids, amino acids, trace elements and lactoserum.

If necessary, the composition of a cosmetic, corporal hygiene or dermopharmaceutical product according to the present invention can be supplemented, to a maximum amount of 2%, with non-biodermal constituents which are cytocompatible with the latter, and which are necessary for the pharmaceutical formulation of the said product, and/or to supplement the topical biological activity of the product. By way of example, mention will be made mainly of fragrances, and quite incidentally and exceptionally certain minor adjuvants required for the correct maintenance of the stability and purity of the cosmetic or dermotherapeutic product.

The biodermal constituents forming virtually all, if not all, of a product according to the invention are formulated and obtained according to traditional techniques, for example in two-phase form, consisting of a water-in-oil or oil-in-water dispersion.

Tables 1 to 3 collate examples of biodermal constituents for formulating an oily phase, and/or an aqueous phase, and supplementing the formulations depending on the applications of the cosmetic product. In these tables, the left-hand column indicates a recommendation, it being understood that, as stated previously, each of the biodermal constituents is by nature cytocompatible with the skin, and biomimetic with the latter. The other columns indicate the class to which the said component belongs, according to the following classification:

Class 1

Substantially cytocompatible and/or bio-assimilable components, present in constitutional form in the skin (water, amino acids, trace elements, vitamins, etc.).

Class 2

Macromolecules obtained by biotechnological means, synthesis or extraction process, which are identical or virtually identical to the constituents of the skin (sodium salt of DNA, sodium hyaluronate, etc.) in composition and structure. These compounds are cytocompatible with the skin, but they can exhibit metabolic interactions in the context of biological or physiological processes. However, their biological action is comparable to that of the components naturally present in the skin (biomimetism).

The components of classes 1 and 2 are interactive, i.e. they act both as active agents and as excipients.

Class 3

Components which are useful to and assimilable by the skin, if possible of food or dietary origin, or alternatively authorized in foodstuffs, but they must be cytocompatible. These components are interactive: they act both as "dermo-dietary" agents and as excipients.

Class 4

Inert components, i.e. components which do not bring about any chemical, biological or immunological effect on the skin: compounds remaining in the superficial cellular strata of the epidermis (for example petroleum jelly and other fatty substances of mineral origin, silicones, titanium dioxide, zinc oxide or mica).

TABLE 1

CUTANEOUS CYTOCOMPATIBILITY SCALE

| NATURE OF THE COMPONENTS | (1) | (2) | (3) | (4) |
|---|---|---|---|---|
| Fluid lipids | oleic acid (XX) linoleic acid (XX) squalene (XX) | triglycerides (XXX) | plant oils (XX or XXX depending on the oil used) | liquid petroleum jelly (XXX) |
| Solid lipids | stearic acid (XX) palmitic acid (XX) cholesterol (XX) cholesterol ester (XX) cholesterol sultate (XX) ceramides (X) | | palm oil (XX) beeswax (XX) | white petroleum jelly (XXX) |
| Radical-scavenging antioxidants | tocopherols (XX) citric acid (XX) glutathione (XX) superoxide dismutase (X) | | bioflavonoids (X) | |
| Preserving agent | taurine (X) | | | |

X     0–1%
XX    1–10%
XXX   10–50%
XXXX  >50%

TABLE 2

| NATURE OF THE COMPONENTS | (1) | (2) | (3) | (4) |
|---|---|---|---|---|
| Surfactants | glycolipids (XX) lecithins (XX) glycosylceramides (XX) lysine stearate (XX) arginine stearate (XX) lysine oleate (XX) | sophorolipids (XX) | lipoproteins (XX) | |
| Thickeners Gelling agents | hyaluronic acid (X) DNA (XX) | mucopolysaccharides (XXX) | xanthan (XXXX) pectin (XX) starch (XX) | chitin (XX) |
| Wetting agents | glycerol (XX) urea (XX) serine (XX) glucose (XX) | | fructose (XX) | |
| Antiseptics | short-chain fatty acids (X) lactoferrin/ lactoperoxidase (X) | | propolis (X) | |

TABLE 3

| NATURE OF THE COMPONENTS | (1) | (2) | (3) | (4) |
|---|---|---|---|---|
| Dyes | vitamin B (X) flavins (X) | | carotenoids (X) caramel (X) | |
| Sunscreens and sunblocks | DNA (XX) pyrimidine bases (XX) melanins (XX) | | | titanium oxide (X) zinc oxide (XX) |
| Fragrances | | | honey (X) | |
| Minerals | sodium (XX) calcium (XX) magnesium (XX) | | | |
| Trace elements | iron, copper (X) zinc (XX) selenium (X) | | | |

The compositions of a number of cosmetic products according to the invention are given below.

PRODUCT 1: Nutrient and moisturizing gel

PHASE A:

| | |
|---|---|
| nutrient composition (amino acids, vitamins, trace elements) | qs 100 |
| sodium salt of DNA | 2–5% |
| preserving system (glucose/glucose oxidase/lactoperoxidase) | 0.9–1.1% |

PHASE B:

| | |
|---|---|
| mucopolysaccharides | 20–30% |
| superoxide dismutase | 0.5–1% |
| citric acid | 0.2–0.5% |
| trisodium citrate | 0.5–2% |

PRODUCT 2: Refreshing and soothing spray

PHASE A:

| | |
|---|---|
| nutrient composition (amino acids, vitamins, trace elements) | qs 100 |
| preserving system (glucose/glucose oxidase/lactoperoxidase) | 0.9–1.1% |

PHASE B:

| | |
|---|---|
| citric acid | 0.2–0.5% |
| trisodium citrate | 0.5–2% |

PHASE C:

| | |
|---|---|
| rhamnose | 0.01–5% |

PRODUCT 3: Radical-scavenging cream (1) for greasy skin

PHASE A:

| | |
|---|---|
| tocopheryl acetate | 0.2–2% |
| stearic acid | 3–5% |
| squalene | 2–7% |
| triglycerides | 2–7% |

PHASE B:

| | |
|---|---|
| water | qs 100 |
| L-arginine | 1–2% |
| glycerol | 1–2% |
| citric acid | 0.2–0.5% |
| trisodium citrate | 0.5–2% |

PHASE C:

| | |
|---|---|
| nutrient composition (amino acids, vitamins, trace elements) | 45–55% |
| preserving system (glucose/glucose oxidase/lactoperoxidase) | 0.9–1.1% |
| superoxide dismutase | 0.5–1% |

PRODUCT 4: Moisturizing cream (2) for dry skin

PHASE A:

| | |
|---|---|
| oleic acid | 0.2–0.3% |
| palmitic acid | 0.2–0.3% |
| behenic acid | 0.2–0.3% |
| stearic acid | 0.1–0.2% |
| linoleic acid | 0.1–0.2% |
| arachidic acid | 0.05–0.1% |
| triglycerides | 0.1–0.2% |
| cholesterol | 0.9–1% |
| cholesterol ester | 0.02–0.04% |
| phospholipids | 1.5–2.5% |
| squalene | 3–7% |

PHASE B:

| | |
|---|---|
| water | qs 100 |
| L-arginine | 1–2% |
| citric acid | 0.2–0.5% |
| trisodium citrate | 0.5–2% |

PHASE C:

| | |
|---|---|
| nutrient composition (amino acids, vitamins, trace elements) | 45–55% |
| preserving system (glucose/glucose oxidase/lactoperoxidase) | 0.9–1.1% |

PHASE D:

| | |
|---|---|
| mucopolysaccharides | 1–3% |

PRODUCT 5: Desensitizing make-up-removing milk

PHASE A:

| | |
|---|---|
| stearic acid | 2–5% |
| squalene | 2–7% |
| triglycerides | 2–7% |

PHASE B:

| | |
|---|---|
| water | qs 100 |
| L-arginine | 1–2% |
| citric acid | 0.2–0.5% |
| trisodium citrate | 0.5–2% |

PHASE C:

| | |
|---|---|
| nutrient composition (amino acids, vitamins, trace elements) | 45–55% |
| superoxide dismutase | 0.5–1% |
| preserving system | 0.9–1.1% |
| fucose | 0.0005–1% |

PRODUCT 6: Moisturizing lotion

PHASE A:

| | |
|---|---|
| water | qs 100 |
| L-serine | 1–3% |

-continued

| | |
|---|---|
| glycerol | 1–2% |
| urea | 1–3% |
| citric acid | 0.2–0.5% |
| trisodium citrate | 0.5–2% |
| PHASE B: | |
| preserving system (glucose/glucose oxidase/lactoperoxidase) | 0.9–1.1% |

PRODUCT 7: Dry oil

PHASE A:

| | |
|---|---|
| squalene | 30–70% |
| triglycerides | 30–70% |

PRODUCT 8: Bioprotective suncream

PHASE A:

| | |
|---|---|
| tocopheryl acetate | 0.2–2% |
| stearic acid | 3–5% |
| squalene | 2–7% |
| triglycerides | 2–7% |
| titanium oxides | 1–20% |
| PHASE B: | |
| water | qs 100 |
| L-arginine | 1–2% |
| glycerol | 1–2% |
| citric acid | 0.2–0.5% |
| trisodium citrate | 0.5–2% |
| PHASE C: | |
| preserving system (glucose/glucose oxidase/lactoperoxidase) | 0.9–1.1% |

PRODUCT 9: Anti-sensitizing and regulating cleansing milk

PHASE A:

| | |
|---|---|
| stearic acid | 2–5% |
| squalene | 2–7% |
| triglycerides | 2–7% |

-continued

| | |
|---|---|
| PHASE B: | |
| water | qs 100 |
| L-arginine | 1–2% |
| glycerol | 1–2% |
| citric acid | 0.2–0.5% |
| trisodium citrate | 0.5–2% |
| PHASE C: | |
| preserving system (glucose/glucose oxidase/lactoperoxidase) | 0.9–1.1% |
| phospholipids | 2–10% |
| PHASE D: | |
| rhamnose | 0.1–5% |
| fucose | 0.0005–1% |

The products according to the invention are, for example, in the form of a lotion, milk, cream, soap, etc., depending on their prescription or use. They are in a stable, single-phase, two-phase or three-phase topical form, for example.

What is claimed is:

1. A cosmetic or corporal hygiene or dermotherapeutic composition comprising:

98–100% by weight of a biodermal fraction including a major biodermal constituent and a minor biodermal constituent, each biodermal constituent being cytocompatible with the skin, the major biodermal constituent including a nutrient composition made of amino acids, vitamins, and trace elements, and the minor biodermal constituent including a mucopolysaccharide; and 0–2% by weight of at least one non-biodermal constituent including a fragrance compatible with the skin.

* * * * *